US 7,811,780 B2

(12) United States Patent
Katayama et al.

(10) Patent No.: US 7,811,780 B2
(45) Date of Patent: Oct. 12, 2010

(54) METHOD FOR MEASUREMENT OF CHOLESTEROL IN HIGH-DENSITY LIPOPROTEIN

(75) Inventors: Yuki Katayama, Mishima (JP); Mayumi Fujinaka, Mishima (JP)

(73) Assignee: Kyowa Medex Co., Ltd., Tokyo (JP)

( * ) Notice: Subject to any disclaimer, the term of this patent is extended or adjusted under 35 U.S.C. 154(b) by 259 days.

(21) Appl. No.: 11/911,029

(22) PCT Filed: Apr. 27, 2006

(86) PCT No.: PCT/JP2006/308850

§ 371 (c)(1), (2), (4) Date: Oct. 9, 2007

(87) PCT Pub. No.: WO2006/118199

PCT Pub. Date: Nov. 9, 2006

(65) Prior Publication Data

US 2009/0280514 A1    Nov. 12, 2009

(30) Foreign Application Priority Data

Apr. 27, 2005    (JP) ............................. 2005-129319

(51) Int. Cl.
*C12Q 1/60*    (2006.01)
(52) U.S. Cl. ....................................................... 435/11
(58) Field of Classification Search .................. 435/11, 435/19, 25, 962
See application file for complete search history.

(56) References Cited

U.S. PATENT DOCUMENTS

| | | | |
|---|---|---|---|
| 4,851,335 A | 7/1989 | Kerscher et al. | |
| 4,892,815 A | 1/1990 | Kerscher et al. | |
| 5,736,406 A * | 4/1998 | Miyauchi et al. | 436/71 |
| 5,773,304 A | 6/1998 | Hino et al. | |
| 5,888,755 A | 3/1999 | Miyauchi et al. | |
| 6,057,118 A * | 5/2000 | Nakamura et al. | 435/11 |
| 6,162,607 A * | 12/2000 | Miki et al. | 435/7.1 |
| 6,630,338 B2 * | 10/2003 | Asai | 435/195 |
| 7,208,287 B2 | 4/2007 | Kishi et al. | |
| 7,544,515 B2 * | 6/2009 | Itoh et al. | 436/71 |
| 2005/0287619 A1 | 12/2005 | Katayama et al. | |
| 2006/0014229 A1 * | 1/2006 | Katayama et al. | 435/11 |

FOREIGN PATENT DOCUMENTS

| | | |
|---|---|---|
| EP | 0 964 249 | 12/1999 |
| EP | 1 555 326 | 7/2005 |
| JP | 08-116996 | 5/1996 |
| JP | 09-000299 | 1/1997 |
| JP | 09-285298 | 11/1997 |
| JP | 9-285298 | * 11/1997 |
| JP | 3869471 | 10/2006 |
| WO | 2004/035816 | 4/2004 |

OTHER PUBLICATIONS

"Cation BB", Unabridged Chemical Dictionary (1997), 482-29 (with translation).
http://www.lookchem.com/cas-112/112-00-5.html, Jun. 30, 2010.

* cited by examiner

*Primary Examiner*—Ralph Gitomer
(74) *Attorney, Agent, or Firm*—Fitzpatrick, Cella, Harper & Scinto

(57) ABSTRACT

The present invention provides a method, a reagent and a kit for the simple and accurate measurement of HDL cholesterol. The method for the measurement of cholesterol in high-density lipoprotein in a sample comprises reacting the sample with i) cholesterol esterase and cholesterol oxidase or ii) cholesterol esterase, oxidized coenzyme and cholesterol dehydrogenase in an aqueous medium comprising a specific nitrogen-containing surfactant having the structure of amine or ammonium salt and a polyanion, and measuring the formed hydrogen peroxide or reduced coenzyme.

7 Claims, No Drawings

METHOD FOR MEASUREMENT OF CHOLESTEROL IN HIGH-DENSITY LIPOPROTEIN

This application is a National Stage application filed under Rule 371 based on PCT/JP2006/308850 filed Apr. 27, 2006, which claims priority to JP 129319/05 filed Apr. 27, 2005.

TECHNICAL FIELD

The present invention relates to a method, a reagent and a kit for the measurement of cholesterol in high-density lipoprotein in a sample.

BACKGROUND ART

Lipoproteins in living systems are classified into high-density lipoprotein (hereinafter abbreviated as HDL), low-density lipoprotein (hereinafter abbreviated as LDL), very low-density lipoprotein (hereinafter abbreviated as VLDL) and chylomicron (hereinafter abbreviated as CM) according to their specific gravity. Each class of lipoprotein has a considerably different function in vivo mainly according to the kind of apoproteins and also has a different lipid composition. It is known that, of these lipoproteins, HDL is involved in the removal of cholesterol accumulated in the cells because it receives cholesterol from tissues including arterial walls and is a risk prevention factor for various kinds of arteriosclerosis, e.g., coronary arteriosclerosis, and therefore, its level in blood is a useful index for predicting the onset of arteriosclerotic diseases.

The conventional methods for the measurement of cholesterol in HDL (hereinafter abbreviated as HDL cholesterol) consist of two operation steps, i.e., fractionation by the ultracentrifugation method, the immunochemical method, the electrophoresis method, the precipitation method, etc. and cholesterol determination. However, the operations of fractionation are complicated and time-consuming and also have a problem in respect of safety. Therefore, the measurement methods containing these separation operations are extremely inefficient and are not suited for practical use.

In recent years, various measurement methods have been proposed to solve the above problems. Examples of the methods include: a method for the fractional determination of HDL cholesterol which comprises reacting serum or plasma with cholesterol esterase and cholesterol oxidase in a buffer comprising the above enzymes, and bile salt, a bile acid derivative or dioctylsulfosuccinate, to allow cholesterol in VLDL and LDL to react with the enzymes prior to the reaction of HDL cholesterol, measuring the formed hydrogen peroxide, and then adding a nonionic surfactant having a polyoxyethylene oxide group to the reaction solution to allow HDL cholesterol to react with the enzymes (see patent document No. 1); and a method for the measurement of HDL cholesterol which comprises reacting serum with pancreas-derived cholesterol esterase and cholesterol oxidase in a buffer comprising the enzymes, a surfactant belonging to the group of bile acids and a nonionic surfactant at a specific pH and a specific temperature (see patent document No. 2). In the method described in patent document No. 2, the reaction of LDL cholesterol with the enzymes proceeds first and then the reaction of HDL cholesterol with the enzymes proceeds, which enables the measurement of HDL cholesterol. However, these methods require a lot of time for measuring and are not always specific for the measurement of HDL cholesterol.

Known examples of the methods for the measurement of HDL cholesterol by aggregating lipoproteins other than HDL include: a method using a reagent for aggregating lipoproteins other than HDL (e.g., dextran sulfate), a divalent metal salt and a chemically modified enzyme (see patent document No. 3); a method using a reagent which forms a complex with lipoproteins other than HDL (e.g., polyanion) and a surfactant which does not dissolve lipoproteins (e.g., polyoxyethylene-polyoxypropylene copolymer) (see patent document No. 4); a method using a polyanion (e.g., dextran sulfate), a divalent metal salt, a specific nonionic surfactant and albumin which is different from the albumin contained in a sample (see patent document No. 5); and a method for the measurement of HDL cholesterol in serum or plasma which comprises treating serum or plasma with a solution containing a lipoprotein fractionating agent (a combination of a polyanion such as dextran sulfate and a divalent cation such as magnesium ion), reacting the obtained mixture with cholesterol esterase and cholesterol oxidase in the presence of an anionic surfactant (alkylsulfonic acid, bile acid or its derivative) without subjecting the mixture to solid-liquid separation, and measuring the formed hydrogen peroxide (see patent document No. 6).

These methods for the measurement of HDL cholesterol by aggregating lipoproteins other than HDL have a good correlation with conventional standard methods. However, there are problems with these methods such as inaccuracy due to turbidity caused by aggregates formed by the reaction, and an excessive load to an autoanalyzer due to deposition of metal hydroxide formed by the reaction with metal salt in a reaction solution when reaction cells are washed with an alkali solution.

Known examples of the methods for the measurement of HDL cholesterol without aggregating lipoproteins other than HDL include: a method for the measurement of HDL cholesterol in a biological sample which comprises reacting the biological sample with pancreas-derived cholesterol esterase and cholesterol oxidase in the presence of bile acid or its salt and albumin, and measuring a compound consumed or formed by the enzymatic reaction (see patent document No. 7); and a method for the measurement of HDL cholesterol in a sample which comprises reacting the sample with lipoprotein lipase which preferentially acts on HDL fraction and/or cholesterol esterase and cholesterol oxidase in the presence of a nonionic surfactant with an HLB value of 16 or more which has reaction selectivity to the HDL fraction (see patent document No. 8). Also known is a method in which cholesterol in lipoproteins other than HDL is preferentially converted into hydrogen peroxide with acyl polyoxyethylene sorbitan ester, and after the formed hydrogen peroxide is eliminated, HDL cholesterol is enzymatically measured by adding polyoxyethylene alkyl ether (see patent document No. 9).

However, these methods for the measurement of HDL cholesterol without aggregating lipoproteins other than HDL sometimes have the problem of inaccuracy of measurement values due to incomplete elimination of cholesterol in lipoproteins other than HDL and non-specific reaction with cholesterol in lipoproteins other than HDL.

Additional known examples of the methods for the measurement of HDL cholesterol without aggregating lipoproteins other than HDL include: a method for the measurement of HDL cholesterol in a sample which comprises reacting the sample with i) cholesterol esterase and cholesterol oxidase or ii) cholesterol esterase, oxidized coenzyme and cholesterol dehydrogenase in an aqueous medium comprising a nonionic surfactant, a polyanion and albumin, and measuring the formed hydrogen peroxide or reduced coenzyme (see patent document No. 10); and a method for the measurement of HDL cholesterol which comprises reacting a sample with cholesterol esterase and cholesterol oxidase, or cholesterol esterase, oxidized coenzyme and cholesterol dehydrogenase in an aqueous medium comprising a bile acid derivative, and measuring the formed hydrogen peroxide or reduced coenzyme (see patent document No. 11).

Patent Document No. 1:
  Japanese Published Unexamined Patent Application No. 69999/87

Patent Document No. 2:
  Japanese Published Unexamined Patent Application No. 126498/88

Patent Document No. 3:
  Japanese Published Unexamined Patent Application No. 131197/96

Patent Document No. 4:
  Japanese Published Unexamined Patent Application No. 201393/96

Patent Document No. 5:
  Japanese Published Unexamined Patent Application No. 285298/97

Patent Document No. 6:
  Japanese Published Unexamined Patent Application No. 116996/96

Patent Document No. 7:
  WO97/40376 pamphlet

Patent Document No. 8:
  WO00/52480 pamphlet

Patent Document No. 9:
  Japanese Published Unexamined Patent Application No. 299/97

Patent Document No. 10:
  WO04/035816 pamphlet

Patent Document No. 11:
  WO04/035817 pamphlet

DISCLOSURE OF THE INVENTION

Problems to be Solved by the Invention

An object of the present invention is to provide a method, a reagent and a kit for the simple and accurate measurement of HDL cholesterol.

Means for Solving the Problems

The present inventors made intensive studies to solve the above problem, have found that cholesterol esterase and cholesterol oxidase or cholesterol dehydrogenase act specifically on HDL in the co-presence of a specific nitrogen-containing surfactant having the structure of amine or ammonium salt and a polyanion, and have completed the present invention.

The present invention relates to the following (1) to (13).

(1) A method for the measurement of cholesterol in high-density lipoprotein in a sample, which comprises: reacting the sample with i) cholesterol esterase and cholesterol oxidase or ii) cholesterol esterase, oxidized coenzyme and cholesterol dehydrogenase in an aqueous medium comprising at least one substance selected from the group consisting of substances represented by general formula (I):

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) and substances represented by general formula (II):

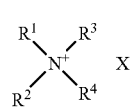

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms) and a polyanion; and measuring the formed hydrogen peroxide or reduced coenzyme.

(2) The method according to the above (1), wherein the aqueous medium further comprises at least one substance selected from the group consisting of albumin, polyoxyethylene alkylamine and polyoxyethylene alkenylamine.

(3) The method according to the above (1) or (2), wherein the polyanion is dextran sulfate or a salt thereof.

(4) A reagent for the measurement of cholesterol in high-density lipoprotein comprising at least one substance selected from the group consisting of substances represented by general formula (I):

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) and substances represented by general formula (II):

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms), a polyanion, cholesterol esterase, cholesterol oxidase and a reagent for the measurement of hydrogen peroxide.

(5) A reagent for the measurement of cholesterol in high-density lipoprotein comprising at least one substance selected from the group consisting of substances represented by general formula (I):

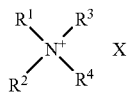

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) and substances represented by general formula (II):

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms), a polyanion, cholesterol esterase, cholesterol dehydrogenase and oxidized coenzyme.

(6) The reagent according to the above (5), further comprising a reagent for the measurement of reduced coenzyme.

(7) The reagent according to any of the above (4) to (6), further comprising at least one substance selected from the group consisting of albumin, polyoxyethylene alkylamine and polyoxyethylene alkenylamine.

(8) The reagent according to any of the above (4) to (7), wherein the polyanion is dextran sulfate or a salt thereof.

(9) A kit for the measurement of cholesterol in high-density lipoprotein comprising a first reagent and a second reagent, which comprises: at least one substance selected from the group consisting of substances represented by general formula (I):

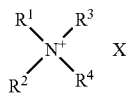

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) and substances represented by general formula (II):

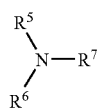

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms) and a polyanion in the first reagent; cholesterol oxidase in the second reagent; a reagent for the measurement of hydrogen peroxide in either or both of the first reagent and the second reagent; and cholesterol esterase in either or both of the first reagent and the second reagent.

(10) A kit for the measurement of cholesterol in high-density lipoprotein comprising a first reagent and a second reagent, which comprises: at least one substance selected from the group consisting of substances represented by general formula (I):

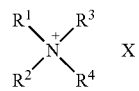

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) and substances represented by general formula (II):

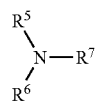

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms) and a polyanion in the first reagent; cholesterol dehydrogenase in the second reagent; oxidized coenzyme in either or both of the first reagent and the second reagent; and cholesterol esterase in either or both of the first reagent and the second reagent.

(11) The kit according to the above (10), further comprising a reagent for the measurement of reduced coenzyme in either or both of the first reagent and the second reagent.

(12) The kit according to any of the above (9) to (11), further comprising at least one substance selected from the group consisting of albumin, polyoxyethylene alkylamine and polyoxyethylene alkenylamine in either or both of the first reagent and the second reagent.

(13) The kit according to any of the above (9) to (12), wherein the polyanion is dextran sulfate or a salt thereof.

EFFECT OF THE INVENTION

The present invention provides a method, a reagent and a kit for the simple and accurate measurement of HDL cholesterol.

BEST MODES FOR CARRYING OUT THE INVENTION

The method for measurement of HDL cholesterol of the present invention is a method for the measurement of HDL cholesterol without eliminating cholesterol in lipoproteins other than HDL or aggregating cholesterol in lipoproteins other than HDL.

Examples of the samples used in the method of the present invention include whole blood, plasma, serum, spinal fluid, saliva, amniotic fluid, urine, sweat and pancreatic juice, among which plasma and serum are preferred.

There is no specific restriction as to the cholesterol esterase used in the present invention so long as it is an enzyme having the ability to hydrolyze cholesterol ester. For example, cholesterol esterase and lipoprotein lipase obtained from animals, plants or microorganisms, and those produced by genetic engineering techniques can be used.

As the cholesterol esterase, both unmodified ones and chemically modified ones can be used, and commercially available ones can also be used.

Examples of the commercially available cholesterol esterases include cholesterol esterase "Amano" 2 (CHE2; Amano Enzyme Inc.), cholesterol esterase "Amano" 3 (CHE3; Amano Enzyme Inc.), lipoprotein lipase (LPL311; Toyobo Co., Ltd.), lipoprotein lipase "Amano" 3 (LPL3; Amano Enzyme Inc.), 43 kDa esterase (Amano Enzyme Inc.), 40 kDa esterase (Amano Enzyme Inc.), EST "Amano" 2 (Amano Enzyme Inc.) and cholesterol esterase [COE313 (chemically modified cholesterol esterase); Toyobo Co., Ltd.). In the present invention, two or more kinds of cholesterol esterases can be used in combination.

Examples of the groups modifying cholesterol esterase (chemically modifying groups) used in chemical modification of cholesterol esterase include a group comprising polyethylene glycol as a main component, a group comprising polypropylene glycol as a main component, a group having a copolymer of polypropylene glycol and polyethylene glycol, a group comprising a water-soluble polysaccharide, a sulfopropyl group, a sulfobutyl group, a polyurethane group and a group having the chelating function, and preferred is a group comprising polyethylene glycol as a main component. Examples of the water-soluble polysaccharides include dextran, pullulan and soluble starch.

Examples of reagents for chemical modification of cholesterol esterase (chemical modifiers) include compounds that have both the above chemically modifying group and a functional group or a structure which can react with an amino group, a carboxyl group, a sulfhydryl group or the like of an enzyme. Examples of the functional groups or structures which can react with an amino group of an enzyme include a carboxyl group, an activated ester group (e.g., N-hydroxysuccinimide group), an acid anhydride, an acid chloride, an aldehyde, an epoxide group, 1,3-propanesultone and 1,4-butanesultone. An example of the functional group or structure which can react with a carboxyl group of an enzyme is an amino group. Examples of the groups or structures reactive with a sulfhydryl group of an enzyme include a maleimide group, a disulfide and α-haloester (e.g., α-iodo ester).

As the chemical modifiers, commercially available ones can be used. Examples of the commercially available chemical modifiers are Sunbright VFM-4101, Sunbright ME-050AS and Sunbright DE-030AS which have a group comprising polyethylene glycol as a main component and an N-hydroxysuccinimide group (all produced by NOF Corporation), Sunbright AKM series (e.g., Sunbright AKM-1510), Sunbright ADM series and Sunbright ACM series which have a group comprising polyalkylene glycol as a main component and an acid anhydride structure (all produced by NOF Corporation), EPOX-3400 and M-EPOX-5000 which have a group comprising polyethylene glycol as a main component and an epoxide group (both produced by Sheawater Polymers), and diethylenetriamine-N,N,N',N'',N''-pentaacetic dianhydride which has a group having the chelating function and an acid anhydride structure (DTPA anhydride, Dojindo Laboratories).

Chemical modification of cholesterol esterase can be carried out, for example, by the following method, but not limited thereto. First, cholesterol esterase is dissolved in a buffer of pH 8.0 or higher (e.g., HEPES buffer), and 0.01 to 500-fold molar amount of a chemical modifier is added thereto at 0 to 55° C., followed by stirring for 5 minutes to 5 hours. In the actual enzymatic reaction, this reaction mixture can be used as such, or if necessary, after removal of the unreacted chemical modifier with an ultrafilter, as the chemically modified cholesterol esterase.

There is no specific restriction as to the concentration of cholesterol esterase used in the method of the present invention, as long as the measurement of HDL cholesterol according to the present invention can be performed. Its concentration in a reaction mixture is preferably 0.01 to 400 U/mL, more preferably 0.02 to 200 U/mL.

There is no specific restriction as to the cholesterol oxidase used in the present invention so long as it is an enzyme having the ability to oxidize cholesterol to form hydrogen peroxide. For example, cholesterol oxidase obtained from animals, plants or microorganisms, and those produced by genetic engineering techniques can be used. Commercially available ones such as cholesterol oxidase "Amano" 1 (CHOD1; Amano Enzyme Inc.), cholesterol oxidase (CHOPE; Kikkoman Corporation), cholesterol oxidase (COO321; Toyobo Co., Ltd.) and cholesterol oxidase Kyowa (Kyowa Hakko Kogyo Co., Ltd.) can also be used. In the present invention, two or more kinds of cholesterol oxidases can be used in combination.

Cholesterol oxidase may be either an unmodified one or a chemically modified one. Chemically modified cholesterol oxidase can be prepared, for example, by the above method for chemical modification using the above chemical modifier.

There is no specific restriction as to the concentration of cholesterol oxidase used in the method of the present invention, as long as the measurement of HDL cholesterol according to the present invention can be performed. Its concentration in a reaction mixture is preferably 0.01 to 400 U/mL, more preferably 0.02 to 200 U/mL.

There is no specific restriction as to the cholesterol dehydrogenase used in the present invention so long as it is an enzyme having the ability to oxidize cholesterol in the presence of oxidized coenzyme to form reduced coenzyme. For example, cholesterol dehydrogenase obtained from animals, plants or microorganisms, and those produced by genetic engineering techniques can be used. Commercially available ones such as cholesterol dehydrogenase "Amano" 5 (CHDH5; Amano Enzyme Inc.) can also be used. In the present invention, two or more kinds of cholesterol dehydrogenases can be used in combination. Cholesterol dehydrogenase may be either an unmodified one or a chemically modified one. Chemically modified cholesterol dehydrogenase can be prepared, for example, by the above method for chemical modification using the above chemical modifier.

There is no specific restriction as to the concentration of cholesterol dehydrogenase used in the method of the present invention, as long as the measurement of HDL cholesterol according to the present invention can be performed. Its concentration in a reaction mixture is preferably 0.01 to 400 U/mL, more preferably 0.02 to 200 U/mL.

In the method using cholesterol dehydrogenase of the present invention, oxidized coenzyme is used. Examples of the oxidized coenzymes are NAD, NADP, thio-NAD and thio-NADP.

In the present invention, a substance represented by general formula (I):

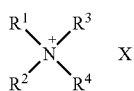

(I)

(wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$, which may be the same or different, each represent a straight-chain or branched alkyl group having 1 to 6 carbon atoms or alkenyl group having 2 to 6 carbon atoms; and X represents an anion) [hereinafter referred to as Compound (I)] or a substance represented by general formula (II):

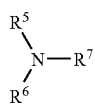

(II)

(wherein $R^5$ represents a straight-chain or branched alkyl group or alkenyl group having 6 to 30 carbon atoms; and $R^6$ and $R^7$, which may be the same or different, each represent a hydrogen atom, or a straight-chain or branched alkyl group having 1 to 30 carbon atoms or alkenyl group having 2 to 30 carbon atoms) [hereinafter referred to as Compound (II)] is used in combination with a polyanion.

The straight-chain or branched alkyl group having 6 to 30 carbon atoms in Compound (I) and Compound (II) includes, for example, hexyl, heptyl, octyl, isooctyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl. Preferred are alkyl groups having 8 to 24 carbon atoms, and more preferred are alkyl groups having 10 to 18 carbon atoms.

The straight-chain or branched alkenyl group having 6 to 30 carbon atoms in Compound (I) and Compound (II) includes, for example, hexenyl, heptenyl, octenyl, nonenyl, decenyl, citronellyl, undecenyl, dodecenyl, tridecenyl, tetradecenyl, pentadecenyl, hexadecenyl, heptadecenyl, oleyl, nonadecenyl, eicosenyl, heneicosenyl, docosenyl, tricosenyl, tetracosenyl, pentacosenyl, hexacosenyl, heptacosenyl, octacosenyl, nonacosenyl and triacontenyl. Preferred are alkenyl groups having 8 to 24 carbon atoms, and more preferred are alkenyl groups having 10 to 18 carbon atoms.

The straight-chain or branched alkyl group having 1 to 30 carbon atoms in Compound (I) and Compound (II) includes, for example, methyl, ethyl, propyl, butyl, pentyl, hexyl, heptyl, octyl, isooctyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl. Preferred are alkyl groups having 1 to 24 carbon atoms, and more preferred are alkyl groups having 1 to 18 carbon atoms.

The straight-chain or branched alkyl group having 1 to 6 carbon atoms in Compound (I) and Compound (II) includes, for example, methyl, ethyl, propyl, butyl, pentyl and hexyl. Preferred are methyl, ethyl and propyl, and more preferred is methyl.

The straight-chain or branched alkenyl group having 2 to 30 carbon atoms in Compound (I) and Compound (II) includes, for example, vinyl, propenyl, allyl, butenyl, pentenyl, hexenyl, heptenyl, octenyl, nonenyl, decenyl, citronellyl, undecenyl, dodecenyl, tridecenyl, tetradecenyl, pentadecenyl, hexadecenyl, heptadecenyl, oleyl, nonadecenyl, eicosenyl, heneicosenyl, docosenyl, tricosenyl, tetracosenyl, pentacosenyl, hexacosenyl, heptacosenyl, octacosenyl, nonacosenyl and triacontenyl. Preferred are alkenyl groups having 2 to 24 carbon atoms, and more preferred are alkenyl groups having 2 to 18 carbon atoms.

The straight-chain or branched alkenyl group having 2 to 6 carbon atoms in Compound (I) and Compound (II) includes, for example, vinyl, propenyl, allyl, butenyl, pentenyl and hexenyl. Preferred are vinyl and propenyl, and more preferred is vinyl.

The anion in Compound (I) includes hydroxide ion, halogen ion, inorganic acid-derived anion and organic acid-derived anion. Examples of the halogen ions are fluoride ion, chloride ion, bromide ion and iodide ion. Examples of the inorganic acid-derived anions are nitrate ion, sulfate ion, phosphate ion and carbonate ion. Examples of the organic acid-derived anions are carboxylate ions such as formate ion, acetate ion, lactate ion, citrate ion and glutamate ion.

Preferred compounds represented by general formula (I) are those wherein $R^1$ represents a straight-chain or branched alkyl group or alkenyl group having 6 to 30 carbon atoms; $R^2$ represents a straight-chain or branched alkyl group having 1 to 30 carbon atoms or alkenyl group having 2 to 30 carbon atoms; $R^3$ and $R^4$ each represent methyl; and X represents an anion.

Specific examples (products) of Compounds (I) are Cation AB, Cation BB, Cation 2ABT, Cation 2 DB-500E and Cation 2-OLR (all produced by NOF Corporation). Specific examples (products) of Compounds (II) are Amine BB, Amine AB, Amine 2-OLR, Tertiary Amine BB and Tertiary Amine FB (all produced by NOF Corporation).

The concentration of Compound (I) or Compound (II) is not specifically limited as long as the measurement of HDL cholesterol according to the present invention can be performed. Its concentration in a reaction mixture is preferably 0.0001 to 1%, more preferably 0.001 to 0.1%.

There is no specific restriction as to the polyanion used in the present invention as long as the measurement of HDL cholesterol according to the present invention can be performed. Examples of the polyanion include dextran sulfate or its salt, heparin or its salt, phosphotungstic acid or its salt, sulfated cyclodextrin or its salt, and sulfated oligosaccharide or its salt, among which dextran sulfate or its salt is preferred. Examples of the dextran sulfate are those with molecular weights of 40,000, 80,000, 200, 000, 500,000, 1,000,000 and 2,000,000. Examples of the sulfated oligosaccharides are sulfated agarose, sulfated trehalose and chondroitin sulfate. Examples of the salts are sodium salt, potassium salt, lithium salt, ammonium salt and magnesium salt. In the present invention, two or more kinds of polyanions may be used. There is no specific restriction as to the concentration of polyanion used in the measurement of HDL cholesterol of the present invention as long as the measurement of HDL cholesterol according to the present invention can be performed. Its concentration in a reaction mixture is preferably 0.001 to 10%, more preferably 0.01 to 1%.

There is no specific restriction as to the albumin used in the present invention as long as the measurement of HDL cholesterol according to the present invention can be performed. Examples of the albumin include albumin obtained from cow, horse, sheep and human, and bovine serum albumin (BSA) is preferred. Albumin produced by genetic engineering techniques can also be used. In the present invention, two or more kinds of albumin can be used in combination. There is no specific restriction as to the concentration of albumin used in the measurement of HDL cholesterol of the present invention as long as the measurement of HDL cholesterol according to the present invention can be performed. Its concentration in a reaction mixture is preferably 0.001 to 10%, more preferably 0.01 to 1%.

Examples of the polyoxyethylene alkylamine or polyoxyethylene alkenylamine used in the present invention include compounds represented by general formula (III):

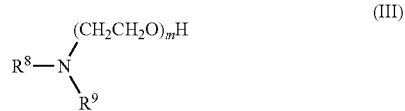

(wherein $R^8$ represents a straight-chain or branched alkyl group or alkenyl group; $R^9$ represents a hydrogen atom or $(CH_2CH_2O)_nH$; and m and n, which may be the same or different, each represent an integer of 1 to 100, and m+n is an integer of 2 to 200) [hereinafter referred to as Compound (III)]. Examples of the alkyl group and alkenyl group in Compound (III) include the above straight-chain or branched alkyl groups having 6 to 30 carbon atoms and the above straight-chain or branched alkenyl groups having 6 to 30 carbon atoms. Preferred are alkyl groups and alkenyl groups having 8 to 24 carbon atoms, and more preferred are alkyl groups and alkenyl groups having 10 to 18 carbon atoms.

Specific examples (products) of the polyoxyethylene alkylamine or polyoxyethylene alkenylamine are Nymeen L201 (oxyethylene dodecylamine; NOF Corporation), Nymeen L207 (polyoxyethylene dodecylamine; NOF Corporation), Nymeen S204, Nymeen S210 (polyoxyethylene octadecylamine; NOF Corporation), Newcol OD420 (polyoxyethylene octadecylamine; Nippon Nyukazai Co., Ltd.), Pionin D3104 (polyoxyethylene laurylamine; Takemoto Oil & Fat Co., Ltd.), Pionin D3110 (polyoxyethylene laurylamine; Takemoto Oil & Fat Co., Ltd.), Pionin D3605 [polyoxyethylene alkyl(soybean)amine; Takemoto Oil & Fat Co., Ltd.], Pionin D3615T [polyoxyethylene alkyl(beef tallow)amine; Takemoto Oil & Fat Co., Ltd.), BLAUNON O209 [polyoxyethylene oleylamino ether; Aoki Oil Industrial Co., Ltd.] and BLAUNON L205 [polyoxyethylene laurylamino ether; Aoki Oil Industrial Co., Ltd.].

The degree of polymerization of the oxyethylene chain of the polyoxyethylene alkylamine and polyoxyethylene alkenylamine is preferably 1 to 100, more preferably 1 to 60. In the present invention, two or more kinds of polyoxyethylene alkylamines and polyoxyethylene alkenylamines may be used. There is no specific restriction as to the concentration of polyoxyethylene alkylamine and polyoxyethylene alkenylamine as long as the measurement of HDL cholesterol according to the present invention can be performed. Their concentration in a reaction mixture is preferably 0.0001 to 1%, more preferably 0.001 to 0.1%.

Examples of the aqueous media used in the method for the measurement of HDL cholesterol of the present invention include deionized water, distilled water and a buffer solution, and preferred is a buffer solution. Examples of the buffers used in the buffer solution are tris(hydroxymethyl)aminomethane buffer, phosphate buffer, borate buffer and Good's buffer.

Examples of Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO) and N-cyclohexyl-3-aminopropanesulfonic acid (CAPS). The concentration of the buffer solution is not specifically limited as long as it is suited for the measurement, but it is preferably 0.001 to 2.0 mol/L, more preferably 0.005 to 1.0 mol/L.

The method, reagent and kit for the measurement of HDL cholesterol of the present invention are specifically described below.

(Method for the Measurement of HDL Cholesterol)

An embodiment of the method for the measurement of HDL cholesterol of the present invention is as follows.

Method for the Measurement

HDL cholesterol in a sample can be measured by:

(1) reacting the sample with cholesterol esterase and cholesterol oxidase, or cholesterol esterase, oxidized coenzyme and cholesterol dehydrogenase in an aqueous medium comprising Compound (I) or Compound (II) and a polyanion, and according to need, at least one substance selected from the group consisting of albumin, polyoxyethylene alkylamine and polyoxyethylene alkenylamine to form hydrogen peroxide or reduced coenzyme;

(2) measuring the formed hydrogen peroxide or reduced coenzyme; and (3) calculating the concentration of HDL cholesterol in the sample from the value measured in (2) and a previously prepared calibration curve.

In the present method, the reaction of (1) is carried out, for example, at 10 to 50° C., preferably 20 to 40° C. for 1 to 60 minutes, preferably 2 to 30 minutes.

The amount of the formed hydrogen peroxide can be measured, for example, directly with a hydrogen peroxide electrode and also by using a reagent for the measurement of hydrogen peroxide. The reagent for the measurement of hydrogen peroxide is a reagent for converting the formed hydrogen peroxide into a detectable substance. Examples of the detectable substances are a dye and luminescence, and preferred is a dye. When the detectable substance is a dye, a reagent for the measurement of hydrogen peroxide comprises an oxidative coloring type chromogen and a peroxidative substance such as peroxidase. Examples of the oxidative coloring type chromogen are oxidative coloring type chromogens described below. When the detectable substance is luminescence, a reagent for the measurement of hydrogen peroxide comprises a chemiluminescent substance. Examples of the chemiluminescent substances are luminol, isoluminol, lucigenin and acridinium ester.

When a reagent comprising an oxidative coloring type chromogen and a peroxidative substance such as peroxidase is used as the reagent for the measurement of hydrogen peroxide, hydrogen peroxide can be determined by subjecting hydrogen peroxide to reaction with an oxidative coloring type chromogen in the presence of a peroxidative substance to form a dye and determining the formed dye. When a reagent for the measurement of hydrogen peroxide comprising a chemiluminescent substance is used, hydrogen peroxide can be determined by subjecting hydrogen peroxide to reaction with the chemiluminescent substance to form photon and determining the formed photon.

Examples of the oxidative coloring type chromogens are leuco-type chromogens and oxidative coupling-type chromogens.

A leuco-type chromogen is a substance that is converted into a dye by itself in the presence of hydrogen peroxide and a peroxidative substance such as peroxidase. Examples of the leuco-type chromogens are 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 4,4'-bis(dimethylamino)diphenylamine and bis[3-bis(4-chlorophenyl)methyl-4-dimethylaminophenyl]amine (BCMA).

An oxidative coupling-type chromogen is a substance that forms a dye by oxidative-coupling of two compounds in the presence of hydrogen peroxide and a peroxidative substance such as peroxidase.

Examples of the combinations of the two compounds include combinations of a coupler and an aniline and combinations of a coupler and a phenol. Examples of the couplers are 4-aminoantipyrine (4-AA) and 3-methyl-2-benzothiazolinone hydrazine. Examples of the aniline are N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxylaniline, N-ethyl-N-(2-hydroxy-3-sulfopropyl) aniline, N-ethyl-N-(3-methylphenyl)-N'-succinylethylenediamine (EMSE), N-ethyl-N-(3-methylphenyl)-N'-acetylethylenediamine and N-ethyl-N-(2-hydroxy-3-sulfopropyl)-4-fluoro-3,5-dimethoxyaniline (F-DAOS). Examples of the phenol are phenol, 4-chlorophenol, 3-methylphenol and 3-hydroxy-2,4,6-triiodobenzoic acid (HTIB).

In the measurement of hydrogen peroxide, the concentration of a peroxidative substance is not specifically limited as long as it is suited for the measurement. When peroxidase is used as the peroxidative substance, its concentration is preferably 1 to 100 kU/L. The concentration of an oxidative coloring type chromogen is not specifically limited as long as it is suited for the measurement, but it is preferably 0.01 to 10 g/L.

Examples of the methods for the measurement of reduced coenzyme are a method in which the absorbance of the formed reduced coenzyme is measured and a method using a reagent for the measurement of reduced coenzyme. In the method comprising the measurement of the absorbance of reduced coenzyme, the absorbance is measured preferably at 300 to 500 nm, more preferably 330 to 400 nm, particularly preferably around 340 nm. The reagent for the measurement of reduced coenzyme is a reagent for converting the formed reduced coenzyme into a detectable substance. An example of the detectable substance is a dye. When the detectable substance is a dye, an example of the reagent for the measurement of reduced coenzyme is a reagent comprising diaphorase, an electron carrier and a reductive coloring type chromogen. An example of the electron carrier is 1-methoxy-5-methylphenazium methylsulfate. When a reagent comprising diaphorase, an electron carrier and a reductive coloring type chromogen is used as the reagent for the measurement of reduced coenzyme, the reduced coenzyme can be determined by measuring a dye formed by the conversion of the reductive coloring type chromogen.

Examples of the reductive coloring type chromogens include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1) and 2-(4-iodophenyl)-3-(2,4-dinitrophenyl)-5-(2,4-disulfophenyl)-2H-tetrazolium monosodium salt (WST-3).

(Reagent for the Measurement of HDL Cholesterol)

In one embodiment of the present invention, the reagent for the measurement of HDL cholesterol comprises at least one substance selected from the group consisting of Compound (I) and Compound (II), a polyanion, cholesterol esterase, cholesterol oxidase and a reagent for the measurement of hydrogen peroxide, and according to need, further comprises at least one substance selected from the group consisting of albumin, polyoxyethylene alkylamine and polyoxyethylene alkenylamine.

Preferred examples of the reagent are: a reagent comprising at least one substance selected from the group consisting of Compound (I) and Compound (II), at least one substance selected from the group consisting of polyoxyethylene alkylamine and polyoxyethylene alkenylamine, a polyanion, cholesterol esterase, cholesterol oxidase and a reagent for the measurement of hydrogen peroxide; and a reagent comprising at least one substance selected from the group consisting of Compound (I) and Compound (II), a polyanion, albumin, cholesterol esterase, cholesterol oxidase and a reagent for the measurement of hydrogen peroxide.

A particularly preferred example is a reagent comprising at least one substance selected from the group consisting of Compound (I) and Compound (II), at least one substance selected from the group consisting of polyoxyethylene alkylamine and polyoxyethylene alkenylamine, a polyanion, albumin, cholesterol esterase, cholesterol oxidase and a reagent for the measurement of hydrogen peroxide.

In another embodiment of the present invention, the reagent for the measurement of HDL cholesterol comprises at least one substance selected from the group consisting of Compound (I) and Compound (II), a polyanion, cholesterol esterase, cholesterol dehydrogenase and oxidized coenzyme, and according to need, further comprises a reagent for the measurement of reduced coenzyme, and at least one substance selected from the group consisting of albumin, polyoxyethylene alkylamine and polyoxyethylene alkenylamine.

Preferred examples of the reagent are: a reagent comprising at least one substance selected from the group consisting of Compound (I) and Compound (II), at least one substance selected from the group consisting of polyoxyethylene alkylamine and polyoxyethylene alkenylamine, a polyanion, cholesterol esterase, cholesterol dehydrogenase, oxidized coenzyme and a reagent for the measurement of reduced coenzyme; and a reagent comprising at least one substance selected from the group consisting of Compound (I) and Compound (II), a polyanion, albumin, cholesterol esterase, cholesterol dehydrogenase, oxidized coenzyme and a reagent for the measurement of reduced coenzyme.

A particularly preferred example is a reagent comprising at least one substance selected from the group consisting of Compound (I) and Compound (II), at least one substance selected from the group consisting of polyoxyethylene alkylamine and polyoxyethylene alkenylamine, a polyanion, albumin, cholesterol esterase, cholesterol dehydrogenase, oxidized coenzyme and a reagent for the measurement of reduced coenzyme.

Certain embodiments of the reagent for the measurement of HDL cholesterol of the present invention are illustrated below, but they are not to be construed as limiting the scope of the present invention. For convenience, at least one substance selected from the group consisting of Compound (I) and Compound (II) is hereinafter referred to as Compound A, and at least one substance selected from the group consisting of albumin, polyoxyethylene alkylamine and polyoxyethylene alkenylamine is hereinafter referred to as Compound B. The reagent of the present invention may comprise one or plural Compounds A and one or plural Compounds B.

Reagent 1
A reagent comprising Compound A, a polyanion, cholesterol esterase, cholesterol oxidase and a reagent for the measurement of hydrogen peroxide Reagent 2
A reagent comprising Compound A, a polyanion, Compound B, cholesterol esterase, cholesterol oxidase and a reagent for the measurement of hydrogen peroxide Reagent 3
A reagent comprising Compound A, a polyanion, cholesterol esterase, oxidized coenzyme and cholesterol dehydrogenase Reagent 4
A reagent comprising Compound A, a polyanion, Compound B, cholesterol esterase, oxidized coenzyme and cholesterol dehydrogenase Reagent 5
A reagent comprising Compound A, a polyanion, cholesterol esterase, oxidized coenzyme, cholesterol dehydrogenase and a reagent for the measurement of reduced coenzyme Reagent 6
A reagent comprising Compound A, a polyanion, Compound B, cholesterol esterase, oxidized coenzyme, cholesterol dehydrogenase and a reagent for the measurement of reduced coenzyme (Kit for the Measurement of HDL Cholesterol)

The reagent for the measurement of HDL cholesterol of the present invention may be preserved, distributed and used in the form of a kit. There is no specific restriction as to the form of a kit, and a kit may be composed of two reagents or three reagents. Preferred is a kit composed of two reagents.

In the kit for the measurement of HDL cholesterol composed of two reagents (a first reagent and a second reagent), cholesterol esterase, and cholesterol oxidase or cholesterol dehydrogenase may be separately contained in the first reagent and the second reagent, or contained together in the second reagent. When they are contained in separate reagents, it is preferred that cholesterol esterase is contained in the first reagent and cholesterol oxidase or cholesterol dehydrogenase is contained in the second reagent. The oxidized coenzyme used in the measurement using cholesterol dehydrogenase may be contained in either or both of the first reagent and the second reagent.

At least one substance selected from the group consisting of Compound (I) and Compound (II) (Compound A) may be contained in either or both of the first reagent and the second reagent, but is preferably contained in the first reagent. A polyanion may be contained in either or both of the first reagent and the second reagent, but is preferably contained in the first reagent.

At least one substance selected from the group consisting of albumin, polyoxyethylene alkylamine and polyoxyethylene alkenylamine (Compound B) may be contained in either or both of the first reagent and the second reagent.

A reagent for the measurement of hydrogen peroxide may be contained in either or both of the first reagent and the second reagent. When the reagent comprises an oxidative coupling-type chromogen, preferred is an embodiment in which the two compounds thereof are respectively contained in separate reagents, that is, an embodiment in which the reagent for the measurement of hydrogen peroxide is contained in both of the first reagent and the second reagent. A reagent for the measurement of reduced coenzyme may be contained in either or both of the first reagent and the second reagent, but is preferably contained in both of the first reagent and the second reagent.

Certain embodiments of the kit for the measurement of HDL cholesterol of the present invention are illustrated below, but they are not to be construed as limiting the scope of the present invention.

Kit 1
First Reagent
Compound A, a polyanion, a reagent for the measurement of hydrogen peroxide and cholesterol esterase
Second Reagent
A reagent for the measurement of hydrogen peroxide and cholesterol oxidase Kit 2
First Reagent
Compound A, a polyanion and a reagent for the measurement of hydrogen peroxide Second Reagent A reagent for the measurement of hydrogen peroxide, cholesterol esterase and cholesterol oxidase Kit 3
First Reagent
Compound A, Compound B, a polyanion, a reagent for the measurement of hydrogen peroxide and cholesterol esterase
Second Reagent
A reagent for the measurement of hydrogen peroxide and cholesterol oxidase Kit 4
First Reagent
Compound A, Compound B, a polyanion and a reagent for the measurement of hydrogen peroxide
Second Reagent
A reagent for the measurement of hydrogen peroxide, cholesterol esterase and cholesterol oxidase Kit 5
First Reagent
Compound A, a polyanion, a reagent for the measurement of hydrogen peroxide and cholesterol esterase
Second Reagent
Compound B, a reagent for the measurement of hydrogen peroxide and cholesterol oxidase Kit 6
First Reagent
Compound A, a polyanion and a reagent for the measurement of hydrogen peroxide
Second Reagent
Compound B, a reagent for the measurement of hydrogen peroxide, cholesterol esterase and cholesterol oxidase Kit 7
First Reagent
Compound A, a polyanion, oxidized coenzyme and cholesterol esterase
Second Reagent
Cholesterol dehydrogenase Kit 8
First Reagent
Compound A, a polyanion and oxidized coenzyme
Second Reagent
Cholesterol esterase and cholesterol dehydrogenase Kit 9
First Reagent
Compound A, Compound B, a polyanion, oxidized coenzyme and cholesterol esterase
Second Reagent
Cholesterol dehydrogenase Kit 10
First Reagent
Compound A, Compound B, a polyanion and oxidized coenzyme
Second Reagent
Cholesterol esterase and cholesterol dehydrogenase Kit 11
First Reagent
Compound A, a polyanion, oxidized coenzyme and cholesterol esterase
Second Reagent
Compound B and cholesterol dehydrogenase Kit 12
First Reagent
Compound A, a polyanion and oxidized coenzyme
Second Reagent
Compound B, cholesterol esterase and cholesterol dehydrogenase Kit 13
First Reagent
Compound A, a polyanion, oxidized coenzyme, a reagent for the measurement of reduced coenzyme and cholesterol esterase
Second Reagent
Cholesterol dehydrogenase Kit 14
First Reagent
Compound A, a polyanion, oxidized coenzyme and a reagent for the measurement of reduced coenzyme
Second Reagent
A reagent for the measurement of reduced coenzyme, cholesterol esterase and cholesterol dehydrogenase Kit 15
First Reagent
Compound A, Compound B, a polyanion, oxidized coenzyme, a reagent for the measurement of reduced coenzyme and cholesterol esterase
Second Reagent
A reagent for the measurement of reduced coenzyme and cholesterol dehydrogenase Kit 16
First Reagent
Compound A, Compound B, a polyanion, oxidized coenzyme and a reagent for the measurement of reduced coenzyme
Second Reagent
A reagent for the measurement of reduced coenzyme, cholesterol esterase and cholesterol dehydrogenase Kit 17
First Reagent
Compound A, a polyanion, oxidized coenzyme, a reagent for the measurement of reduced coenzyme and cholesterol esterase
Second Reagent
Compound B, a reagent for the measurement of reduced coenzyme and cholesterol dehydrogenase Kit 18
First Reagent
Compound A, a polyanion, oxidized coenzyme and a reagent for the measurement of reduced coenzyme
Second Reagent
Compound B, a reagent for the measurement of reduced coenzyme, cholesterol esterase and cholesterol dehydrogenase In the reagent and the kit for the measurement of HDL cholesterol of the present invention, the following components which are described in the above description of the method for the measurement of HDL cholesterol of the present invention can be used: Compound (I), Compound (II), a polyanion, albumin, polyoxyethylene alkylamine, polyoxyethylene alkenylamine, cholesterol esterase, cholesterol oxidase, cholesterol dehydrogenase, oxidized coenzyme, a reagent for the measurement of hydrogen peroxide and a reagent for the measurement of reduced coenzyme.

The reagent and the kit for the measurement of HDL cholesterol of the present invention may comprise, according to need, an aqueous medium, a stabilizer, an antiseptic, an interference inhibitor, a reaction promoter, etc. Examples of the aqueous media are the above-mentioned aqueous media. Examples of the stabilizers are ethylenediaminetetraacetic acid (EDTA), sucrose and calcium chloride. Examples of the antiseptics are sodium azide and antibiotics. An example of the interference inhibitor is ascorbate oxidase to inhibit the effect of ascorbic acid. Examples of the reaction promoters are enzymes such as colipase and phospholipase, and salts such as sodium sulfate and sodium chloride.

The reagent and the kit for the measurement of HDL cholesterol of the present invention may be in freeze-dried form or in a state of being dissolved in an aqueous medium. When HDL cholesterol in a sample is measured using the reagent in freeze-dried form, the reagent is used after being dissolved in an aqueous medium.

Cholesterol esterase, cholesterol oxidase and cholesterol dehydrogenase are contained in the reagent and the kit for the measurement of HDL cholesterol of the present invention in such amount that the concentration thereof in an aqueous medium becomes preferably 0.01 to 1200 U/mL, more preferably 0.02 to 600 U/mL.

Compound (I) or Compound (II) is contained in the reagent and the kit for the measurement of HDL cholesterol of the present invention in such amount that the concentration thereof in an aqueous medium becomes preferably 0.0001 to 3%, more preferably 0.001 to 0.3%. A polyanion is contained in the reagent and the kit for the measurement of HDL cholesterol of the present invention in such amount that the concentration thereof in an aqueous medium becomes preferably 0.001 to 30%, more preferably 0.01 to 3%.

Albumin is contained in the reagent and the kit for the measurement of HDL cholesterol of the present invention in such amount that the concentration thereof in an aqueous medium becomes preferably 0.001 to 30%, more preferably 0.01 to 3%.

Polyoxyethylene alkylamine or polyoxyethylene alkenylamine is contained in the reagent and the kit for the measurement of HDL cholesterol of the present invention in such amount that the concentration thereof in an aqueous medium becomes preferably 0.0001 to 3%, more preferably 0.001 to 0.3%.

Certain specific embodiments of the present invention are illustrated in the following examples, which are not to be construed as limiting the scope of the present invention. Reagents and enzymes used in the examples are products from the following manufacturers. HEPES (BDH Laboratory), EMSE (Daito Chemix Corporation), sodium sulfate (Kanto Chemical Co., Inc.), Amine BB (dodecylamine; NOF Corporation), Tertiary Amine BB (dodecyl dimethylamine; NOF corporation), Cation BB (dodecyl trimethyl ammonium chloride; NOF Corporation), sodium dextran sulfate (molecular weight: 500,000; Pharmacia), bovine serum albumin (BSA; Proliant Inc.), 4-aminoantipyrine (Salkyo Kasei Co., Ltd.), peroxidase (Toyobo Co., Ltd.), 43 kDa esterase (cholesterol esterase; Amano Enzyme Inc.), CHOPE (cholesterol oxidase; Kikkoman Corporation) and BLAUNON L205 (polyoxyethylene laurylamino ether; Aoki Oil Industrial Co., Ltd.)

Example 1

A kit for the measurement of HDL cholesterol comprising the following first reagent (Reagent A) and second reagent (Reagent a) was prepared.

| First reagent (Reagent A) | |
|---|---|
| HEPES (pH 7.5) | 10 mmol/L |
| EMSE | 0.3 g/L |
| Sodium sulfate | 5.0 g/L |
| Amine BB | 0.1 g/L |
| Sodium dextran sulfate | 1.0 g/L |

| Second reagent (Reagent a) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |

Example 2

A kit for the measurement of HDL cholesterol comprising the following first reagent (Reagent B) and second reagent (Reagent a) was prepared.

| First reagent (Reagent B) | |
|---|---|
| HEPES (pH 7.5) | 10 mmol/L |
| EMSE | 0.3 g/L |
| Sodium sulfate | 5.0 g/L |
| Tertiary Amine BB | 0.03 g/L |
| Sodium dextran sulfate | 1.0 g/L |

| Second reagent (Reagent a) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |

Example 3

A kit for the measurement of HDL cholesterol comprising the following first reagent (Reagent C) and second reagent (Reagent a) was prepared.

| First reagent (Reagent C) | |
|---|---|
| HEPES (pH 7.5) | 10 mmol/L |
| EMSE | 0.3 g/L |
| Sodium sulfate | 5.0 g/L |
| Cation BB | 0.14 g/L |
| Sodium dextran sulfate | 1.0 g/L |

| Second reagent (Reagent a) | |
|---|---|
| HEPES (pH 7.0) | 10 mmol/L |
| 4-Aminoantipyrine | 0.3 g/L |

-continued

| Second reagent (Reagent a) | |
|---|---|
| Peroxidase | 20 kU/L |
| 43 kDa esterase | 100 kU/L |
| CHOPE | 1.2 kU/L |

Example 4

A kit for the measurement of HDL cholesterol comprising the following first reagent (Reagent D) and second reagent (Reagent a) was prepared.

| First reagent (Reagent D) | |
|---|---|
| HEPES (pH 7.5) | 10 mmol/L |
| EMSE | 0.3 g/L |
| Sodium sulfate | 5.0 g/L |
| Cation BB | 0.14 g/L |
| Sodium dextran sulfate | 1.0 g/L |
| BSA | 2.0 g/L |

| Second reagent (Reagent a) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |

Example 5

A kit for the measurement of HDL cholesterol comprising the following first reagent (Reagent C) and second reagent (Reagent b) was prepared.

| First reagent (Reagent C) | |
|---|---|
| HEPES (pH 7.5) | 10 mmol/L |
| EMSE | 0.3 g/L |
| Sodium sulfate | 5.0 g/L |
| Cation BB | 0.14 g/L |
| Sodium dextran sulfate | 1.0 g/L |

| Second reagent (Reagent b) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |
| BLAUNON L205 | 0.16 g/L |

Example 6

A kit for the measurement of HDL cholesterol comprising the following first reagent (Reagent D) and second reagent (Reagent b) was prepared.

| First reagent (Reagent D) | |
|---|---|
| HEPES (pH 7.5) | 10 mmol/L |
| EMSE | 0.3 g/L |
| Sodium sulfate | 5.0 g/L |
| Cation BB | 0.14 g/L |
| Sodium dextran sulfate | 1.0 g/L |
| BSA | 2.0 g/L |

| Second reagent (Reagent b) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |
| BLAUNON L205 | 0.16 g/L |

Comparative Example 1

A kit for the measurement of HDL cholesterol comprising the following first reagent (Reagent E) and second reagent (Reagent a) was prepared.

| First reagent (Reagent E) | |
|---|---|
| HEPES (pH 7.5) | 10 mmol/L |
| EMSE | 0.3 g/L |
| Sodium sulfate | 5.0 g/L |
| Sodium dextran sulfate | 1.0 g/L |

| Second reagent (Reagent a) | |
|---|---|
| HEPES (pH 7.0) | 10 mmol/L |
| 4-Aminoantipyrine | 0.3 g/L |
| Peroxidase | 20 kU/L |
| 43 kDa esterase | 100 kU/L |
| CHOPE | 1.2 kU/L |

Example 7

Measurement of HDL cholesterol in human serum (30 samples) was carried out using the kit of Example 1.

(1) Preparation of a Calibration Curve

A calibration curve which shows the relationship between the HDL cholesterol concentration and "the absorbance" was prepared using a physiological saline (HDL cholesterol concentration: 0.0 mg/dL) and a serum (HDL cholesterol concentration: 80.0 mg/dL) as standard solutions, the kit of Example 1, and Hitachi-7170S autoanalyzer.

"The absorbance" herein refers to the value obtained based on the two absorbances (E1 and E2) measured in the following reaction and by subtracting E1 from E2.

To a reaction cell were added a standard solution (2 μL) and the first reagent (0.15 mL), and the resulting mixture was incubated at 37° C. for 5 minutes. The absorbance of the reaction mixture (E1) was measured at a main wavelength of 600 nm and a sub-wavelength of 700 nm. Then, the second reagent (0.05 mL) was added to the reaction mixture, followed by further incubation at 37° C. for 5 minutes, and the absorbance of the reaction mixture (E2) was measured at a main wavelength of 600 nm and a sub-wavelength of 700 nm.

(2) Calculation of "the Absorbance" of Human Serum Samples Obtained by the Reaction of the Samples with the Kit of Example 1

"The absorbance" of the samples was calculated in the same manner as in the calculation method of "the absorbance" of (1), except that the human serum samples were used in place of the standard solutions used in the preparation of the calibration curve of (1).

(3) Measurement of the Concentration of HDL Cholesterol in Human Serum Samples

The concentration of HDL cholesterol in each of the samples was measured from "the absorbance" calculated in (2) and the calibration curve prepared in (1).

Example 8

The HDL cholesterol in each of the human serum samples (30 samples) was measured on Hitachi-7170 autoanalyzer in the same manner as in Example 7, except that the kit of Example 2 was used in place of the kit of Example 1.

Example 9

The HDL cholesterol in each of the human serum samples (30 samples) was measured on Hitachi-7170 autoanalyzer in the same manner as in Example 7, except that the kit of Example 3 was used in place of the kit of Example 1.

Example 10

The HDL cholesterol in each of the human serum samples (30 samples) was measured on Hitachi-7170 autoanalyzer in the same manner as in Example 7, except that the kit of Example 4 was used in place of the kit of Example 1.

Example 11

The HDL cholesterol in each of the human serum samples (30 samples) was measured on Hitachi-7170 autoanalyzer in the same manner as in Example 7, except that the kit of Example 5 was used in place of the kit of Example 1

Example 12

The HDL cholesterol in each of the human serum samples (30 samples) was measured on Hitachi-7170 autoanalyzer in the same manner as in Example 7, except that the kit of Example 6 was used in place of the kit of Example 1.

Comparative Example 2

The HDL cholesterol in each of the human serum samples (30 samples) was measured on Hitachi-7170 autoanalyzer in the same manner as in Example 7, except that the kit of Comparative Example 1 was used in place of the kit of Example 1.

Then, the HDL cholesterol in each of the human serum samples (30 samples) used in the measurement of Examples 7 to 12 and Comparative Example 2 was measured by the DCM method (Designated Comparison Method) described in Clinical Chemistry, Vol. 45, No. 10 (1999), and the measurement values were compared with those obtained in the Examples and the Comparative Example. The correlation coefficients between each of the measurements of the Examples and the Comparative Example and the measurement by the DCM method are shown in Table 1.

TABLE 1

| Method for measurement | Measurement kit | | Correlation coefficient |
|---|---|---|---|
| | First reagent | Second reagent | |
| Comparative Example 2 | Comparative Example 1 Reagent E | Reagent a | 0.191 |
| Example 7 | Example 1 Reagent A | Reagent a | 0.792 |
| Example 8 | Example 2 Reagent B | Reagent a | 0.892 |
| Example 9 | Example 3 Reagent C | Reagent a | 0.826 |
| Example 10 | Example 4 Reagent D | Reagent a | 0.973 |
| Example 11 | Example 5 Reagent C | Reagent b | 0.900 |
| Example 12 | Example 6 Reagent D | Reagent b | 0.991 | lp;1pFrom the comparison of Comparative Example 2 and Examples 7 to 12 shown in Table 1, it was revealed that a good correlation with DCM was recognized in the measurement using the kits comprising Compound (I) or Compound (II) and a polyanion. It was further revealed from the comparison of Example 9 and Examples 10 to 12 that the correlation coefficient with DCM was improved by allowing albumin or polyoxyethylene alkylamine to be present in addition to Compound (I) or Compound (II) and a polyanion.

INDUSTRIAL APPLICABILITY

The present invention provides a method, a reagent and a kit for the measurement of HDL cholesterol which are useful for the diagnosis of diseases such as arteriosclerosis.

The invention claimed is:

1. A method for measuring a concentration of cholesterol in high-density lipoprotein (HDL) in a sample, which comprises:
    (1) reacting the sample, in an aqueous medium comprising dodecyltrimethylammonium chloride and a polyanion, with enzymes selected from the group consisting of
        i) a combination of cholesterol esterase and cholesterol oxidase, and
        ii) a combination of cholesterol esterase, oxidized coenzyme and cholesterol dehydrogenase;
    (2) measuring formed hydrogen peroxide or reduced coenzyme to obtain a value; and
    (3) correlating the value obtained in step (2) with the concentration of HDL cholesterol based on a previously prepared calibration curve.

2. The method according to claim 1, wherein the aqueous medium further comprises at least one substance selected from the group consisting of albumin, polyoxyethylene alkylamine and polyoxyethylene alkenylamine.

3. The method according to claim 1 or 2, wherein the polyanion is dextran sulfate or a salt thereof.

4. The method according to claim 1 or 2, wherein said aqueous medium contains said dodecyltrimethylammonium chloride at a concentration of 0.0001-1% and said polyanion at a concentration of 0.001-10%.

5. The method according to claim 3, wherein said aqueous medium contains said dodecyltrimethylammonium chloride at a concentration of 0.0001-1% and said polyanion at a concentration of 0.001-10%.

6. The method according to claim 4, wherein said aqueous medium contains said dodecyltrimethylammonium chloride at a concentration of 0.001-0.1% and said polyanion at a concentration of 0.01-1%.

7. The method according to claim 5, wherein said aqueous medium contains said dodecyltrimethylammonium chloride at a concentration of 0.001-0.1% and said polyanion at a concentration of 0.01-1%.

* * * * *